(12) United States Patent
Sacchi et al.

(10) Patent No.: US 8,993,748 B2
(45) Date of Patent: *Mar. 31, 2015

(54) PROCESS FOR THE PREPARATION OF TRIVALENT IRON COMPLEXES WITH MONO-, DI- AND POLYSACCHARIDE SUGARS

(71) Applicant: BIOFER S.p.A., Medolla (Modena) (IT)

(72) Inventors: Stefania Sacchi, Carpi (IT); Mauro Montorsi, Modena (IT); Egidio Marchi, Casalecchio di Reno (IT)

(73) Assignee: BIOFER S.p.A., Medolla (Modena) (IT)

( * ) Notice: Subject to any disclaimer, the term of this patent is extended or adjusted under 35 U.S.C. 154(b) by 0 days.

This patent is subject to a terminal disclaimer.

(21) Appl. No.: 14/223,752

(22) Filed: Mar. 24, 2014

(65) Prior Publication Data

US 2014/0296508 A1 Oct. 2, 2014

Related U.S. Application Data

(62) Division of application No. 11/908,575, filed as application No. PCT/IB2006/000560 on Mar. 14, 2006, now Pat. No. 8,759,320.

(30) Foreign Application Priority Data

Mar. 15, 2005 (IT) .............. MO2005A0056

(51) Int. Cl.
  *C07H 23/00* (2006.01)
  *C08B 37/02* (2006.01)
  *C07H 1/00* (2006.01)
  *C08B 30/18* (2006.01)
  *C08B 31/00* (2006.01)

(52) U.S. Cl.
  CPC ............... *C07H 23/00* (2013.01); *C07H 1/00* (2013.01); *C08B 30/18* (2013.01); *C08B 31/00* (2013.01); *C08B 37/0021* (2013.01)
  USPC .......................................... 536/113; 536/121

(58) Field of Classification Search
  CPC .... C08B 30/18; C08B 37/0021; C08B 31/00; C07H 1/00; C07H 23/00
  USPC ................................................. 536/113, 121
  See application file for complete search history.

(56) References Cited

U.S. PATENT DOCUMENTS

| | | | |
|---|---|---|---|
| 2,820,740 | A | 1/1958 | London et al. |
| 2,885,393 | A | 5/1959 | Herb |
| 3,574,184 | A | 4/1971 | Ranulph et al. |
| 4,180,567 | A | 12/1979 | Herb |
| 4,370,476 | A | 1/1983 | Usher et al. |
| 4,599,405 | A | 7/1986 | Muller et al. |
| 4,749,695 | A | 6/1988 | Schwengers |
| 4,788,281 | A | 11/1988 | Tosoni et al. |
| 5,326,864 | A | 7/1994 | Besemer et al. |
| 5,756,715 | A | * 5/1998 | Monte et al. ............. 536/113 |
| 6,291,440 | B1 | 9/2001 | Andreasen et al. |
| 6,498,269 | B1 | 12/2002 | Merbouh et al. |
| 6,977,249 | B1 | 12/2005 | Andreasen et al. |

FOREIGN PATENT DOCUMENTS

| | | | |
|---|---|---|---|
| DE | 461 370 | 6/1928 | |
| DE | 461370 | * 6/1928 | ............ C07C 59/105 |
| EP | 0 150 085 | 7/1985 | |
| WO | WO 97/17377 | 5/1997 | |
| WO | WO 00/30657 | 6/2000 | |
| WO | WO 2004/037865 | 5/2004 | |

OTHER PUBLICATIONS

Besemer et al, Starch/Starke 1994, 3, pp. 95-101.*
Besemer, Arie C. et al., "The Relation between Calcium Sequestering Capacity and Oxidation Degree of DicarboxyStarch and Dicarboxy-Inulin", Starch/Starke, Wiley-Vch Verlag, Weinheim, DE, vol. 46, No. 11, Nov. 1, 1994, pp. 419-422, XP000474356, ISSN: 0038-9056.
De Nooy, Arjan E.J. et al., "On the Use of Stable Organic Nirtoxyl Radicals for the Oxidation of Primary and Secondary Alcohols", Synthesis, (10), pp. 1153-1174, CODEN: SYNTBF; ISSN: 0039-7881,1996, XP009071799.
Besemer, Arie C. et al., "Dicarboxy-Starch by Sodium Hypochlorite/Bromide Oxidation and Its Calcium Binding Properties", Starch/Staerke, vol. 46, No. 3, pp. 95-101, CODEN: STARDD; ISSN: 0038-9056,1994, XP009071785.
Besemer, Arie C. et al., "The hypochlorite oxidation of inulin", Recueil Des Travaux Chimiques Des Paysbas, vol. 113, No. 9, pp. 398-402, CODEN: RTCPA3; ISSN: 0165-0513,1994, XP009071783.
Besemer, Arie C. et al., "The Catalytic Effect of Bromide in the Hypochlorite Oxidation of Linear Dextrins and Inulin", Starch/Staerke, vol. 46, No. 3, pp. 101-106, CODEN: STARDD; ISSN: 0038-9056,1994, XP009071995.
Deary, Michael E. et al., "Evidence for cyclodextrin dioxiranes", Carbohydrate Research, Elsevier Scientific Publishing Company, Amsterdam, NL, vol. 309, No. 1, Jun. 1998, pp. 17-29, XP004130091, ISSN: 0008-6215.
Kardos, Nathalie et al., "Sonochemistry of carbohydrate compunds", Carbohydrate Research, Elsevier Scientific Publishing Company, Amsterdam, NL, vol. 332, No. 2, May 18, 2001, pp. 115-131, XP004239845 ISSN: 0008-6215.
Anelli, Pier Lucio et al., "Fast and Selective Oxidation of Primary Alcohols to Aldehydes or to Carboxylic Acids and of Secondary Alcohols to Ketones Mediated by Oxoammonium Salts under Two-Phase Condititons", Journal of Organic Chemistry, vol. 52, No. 12, pp. 2559-2562, CODEN: JOCEAH; ISSN: 0022-3263, 1987, XP002397801.
Search Report issued by the European Patent Office in corresponding Application No. PCT/IB2006/000560, mailed Sep. 27, 2006.
Loudon, G. Marc, "Organic Chemistry," $3^{rd}$ Ed., 1995, p. 1349.

* cited by examiner

*Primary Examiner* — Ganapathy Krishnan
(74) *Attorney, Agent, or Firm* — Greer Burns & Crain, Ltd.

(57) ABSTRACT

Process for the preparation of trivalent iron complexes with mono-, di- and polysaccharide sugars, consisting of the activation of the sugar by oxidation with nascent bromine generated in situ by reaction between an alkaline or alkaline earth bromine and an alkaline hypochlorite, the complexation of the activated sugar in solution with a ferric salt dissolved in an aqueous solution, the purification of the resulting solution through ultrafiltration and finally the stabilization of the trivalent iron-sugar complex by heating at a temperature between 60° C. and 100° C. for a period between 1 and 4 hours at a pH between 9.0 and 11.0.

20 Claims, 1 Drawing Sheet

PROCESS FOR THE PREPARATION OF TRIVALENT IRON COMPLEXES WITH MONO-, DI- AND POLYSACCHARIDE SUGARS

AMBIT OF THE INVENTION

The aim of the present invention relates to the synthesis of trivalent iron (III) complexes with mono-, di- and polysaccharide sugars. The products obtainable according to the method of the present patent can be: iron gluconate, iron polymaltose, iron dextran, iron saccharate stabilized with sucrose, or novel complexes such as the iron lactate or other.

These derivatives can be advantageously used in the therapy of different pathologies, such as
 functional iron deficiency in patients suffering from a renal chronic failure;
 bad absorption of the iron due to intestinal diseases;
 chronic blood loss also together with erythropoietin;
 constitutional anemia.

The synthesis of the trivalent iron complexes with sugars is known since many years even if, still today, the research in this field is active, as several methods used for the synthesis lead to not much stable complexes or said methods are difficult to apply.

It should be remembered that the iron complexes are produced above all for being orally, intramuscularly or intravenously administered to patients or animals, as suitable drugs for preventing or treating pathologies from iron deficiency.

For this reason, these iron derivatives must have some fundamental characteristics, such as: physical-chemical stability over time, safety in the administration, low toxicity, good bioavailability and easiness of production.

As for the toxicity and the bioavailability, it is known that the bivalent iron has an optimal oral bioavailability but has as well an intrinsic toxicity which is expressed at a gastrointestinal and hepatic level, above all due to the accumulation. For these reasons, the bivalent iron salts are not much used in therapy, even if the production cost is limited and can be orally administered, moreover the sideremy level reached with the therapy must always be accurately monitored. On the contrary, the trivalent iron is less toxic when is administered in products which effectively stabilize the iron through complexation of the same, as it occurs at a biological level for example by the ferritin, which complexes the iron but maintains a good capability of giving it to the biological systems assigned for transporting or using the same. The trivalent iron is a strong oxidant and so, if not trapped in systems capable of storing and giving it only when effectively required by the endocrine system, it can seriously damage some important organs, such as the liver and the kidneys.

From above, it is evicted that the complex must have an opportune stability which has to ensure, from one side, the required preservation of the product in vials and from the other side, the equally important capability of delivering the iron only to the proteinic systems intended to the depot storage or the transport of the iron itself. Therefore, the stability of the $Fe^{+++}$-sugar complex is one of the most important features, because from this depends not only the shelf life of the selected pharmaceutical form but also the bioavailability of the complexed iron. A poorly stable complex will cause great problems, not only about the administration but also the toxicity, as it will deliver the iron to all the biological Systems capable of producing complexes with the iron, for example the hematic proteins, by subtracting it to the biological systems specifically assigned to the transport and the storage of the same.

It has been noted that the trivalent iron complex with the sugars is stable if some essential conditions are respected:

1) physical-chemical homogeneity of the ferric hydroxide
 2) Use of polysaccharides with a low content of low molecular weights
 3) Sugars with the activated glucoside terminus.

1) The first condition is that the ferric hydroxide must be a homogeneous product, namely it must not be a mixture of polymorph forms which can complex the iron in a different way, each with a different stability. Furthermore, the ferric hydroxide must not be charged and therefore it must not be even partially salified with anions, a thing that can happen when one tries to isolate it from a solution of a salt thereof by basic treatment.

For example, the precipitation, in addition to $Fe(OH)_3$, of $FE(OH)_2Cl$, or $NaFe(OH)_2CO$ and so on can occur, obtaining mixtures of hydroxides which make difficult the complex formation and decrease the stability thereof.

Erni I, et al. *Arzneim.-Forsch./Drug. Res.* 34, (II), No. 11 p. 1555-1558, 1984, state that the precipitated and isolated ferric hydroxide, even if in controlled and repetitive reaction conditions, always consists of different kinds of hydroxides.

All the above is confirmed by the fact that the ferric hydroxide, which is reacted with the sugar, is only partly solubilized and forms the complex by remaining partly as a bottom body or, as it often happens, precipitating the complex after a time. Therefore, in order to obtain an effective and repeatable reaction for the complex formation, it is necessary to carry out the iron hydration reaction in a solution, allowing the reaction itself to slowly re-equilibrate in the presence of sugar.

Moreover, everyone knows that the isolation and the purification of the ferric hydroxide are two steps that have a remarkable productive difficult.

2) The second condition is that the sugar should be activated, namely the end group should not be in form of aldehyde or hemiacetal. In fact, this end group besides being unable to participate to the formation of the complex, can intervene by partly reducing the trivalent iron bringing it to the lower oxidation state of bivalent iron, which is largely bioavailable also by mouth, but just for this reason becomes particularly harmful for the organism, requiring a constant monitoring of the hematic levels.

Therefore, if the polyhydroxylate compound that one whishes to use for forming the complex with the iron contains some reducing end groups, such as an aldohexose sugar, since such groups can destabilize the complex, it is necessary that the aldehyde group, also in form of hemiacetal form, is transformed in a stable group which can contribute to the formation and stabilization of the complex with the Fe. The more suitable transformations of the aldehyde end group are the reduction to an alcohol group or the oxidation to a carboxy group. This operation is called sugar "activation".

The conditions applied to various synthesis described in the patents do not foresee an alteration of the sugar, however the complex formation is carried out in a basic environment at high temperature, whereby in such conditions the end groups can likely undergo a modification similar to the one described by Cannizzaro for the adehydes subjected to dismutation in a basic environment. However, in these conditions the sugar itself can undergo different degradation reactions.

In many other patents, sugar previously activated in a basic environment at high temperature is used. These conditions, even if less destroying than the preceding ones as the reaction takes place in absence of iron, lead however to a mixture wherein, together with a sugar in which the acetal group is partly oxidized to acid and partly reduced to 7 alcohol, modified and hydrolized sugars can be obtained, as it can be ascertained by the dark colour of the solution and the strong caramel smell.

Other patents report a sugar activation through oxidation with bromine, bromites or chlorites which however represent reagents of a difficult handling, preparation and storage. Moreover, it is known that the use of such reagents, if not carried out in controlled pH conditions, reagent concentration and temperature, can lead to oxidation reactions driven with partial hydrolysis of the end sugar.

3) The third condition, in case of polysaccharide sugars, is that the sugar used should not contain very low molecular weight fractions, as these are able to complex a large quantity of iron but are unable to ensure the solubility of the complex. In fact, gelation phenomena of the solution or precipitation of a bottom body which effectively prevents the parenteral administration of the preparation can occur over time in preparations with a high content of very low molecular weights.

Generally, iron complexes with activated mono- or disaccharide sugars are stabilized by increasing the pH and introducing in the preparation large quantities of sugar. These complexes have a pH between 8.0 and 12.0 and therefore are administered only intravenously. Also sugars with too high molecular weights are harmful for the formation of the complex with the iron. Especially in case of dextran, the very high molecular weights can cause anaphylactic shock and increase the general toxicity of the complex, above all when administered by parenteral route.

It is therefore necessary to evaluate with a great attention the contents of high and low molecular weights, and for this reason there are some patents which claim sugars with particular molecular weights or ranges of molecular weight.

By analyzing the state of the art, it is possible to find several patents which report different synthesis systems wherein the three conditions above considered are completely or partly disregarded.

Many patents report, for example, the synthesis of iron/polysaccharides complexes starting from isolated ferric hydroxide, such as the U.S. Pat. No. 4,180,567 wherein dialyzed ferric hydroxide and non-activated dextran, dextrins or glucose are used as complexing agents, or the patent Fr 1,462,959, wherein ferric hydroxide and sorbitol are Used as complexing agents. Also in the U.S. Pat. No. 4,749,695 ferric hydroxide is reacted. with dextran at a high temperature, while in the patent GB 694,452 the isolated ferric hydroxide is reacted with cane sugar. The obtained product is precipitated and heated in a high temperature oven, and such synthesis leads to non-standardized and sometimes even toxic products.

On the contrary, there are several patents which, for obtaining the complexes in question, use trivalent iron salts in an aqueous solution, then the sugar is added by simultaneously rising the pH and the temperature. If the rising of the pH is gradually carried out, there can be a re-balance between all the variously hydrated intermediate compounds of the iron, namely, for example, starting from iron trichloride, by slowly increasing the pH a slow re-balance of $FeCl_3$ to $FeCl_2OH$ then to $FeCl(OH)_2$ to $Fe(OH)_3$ or $FeOOH$ is obtained, depending on the final pH. It should be kept in mind that also other balance intermediate forms are possible, such as $NaFeCO_3(OH)_2$ if hydrogen carbonate or carbonate is used for increasing the pH. As above mentioned, the obtainment step of the ferric hydroxide, which being insoluble precipitates together with their balance forms, is determinant. A sharp increase of the pH leads to the obtainment of a ferric hydroxide which co-precipitates with all its balance components, since these latter are not able to re-balance themselves in favour of the end product, i.e. the ferric hydroxide.

In many patents the sugar is not activated before its reaction with the ferric hydroxide, but it should be kept in mind that the aldohexose sugars, even if they have the aldehyde end group in form of hemiacetal, when subjected to a strong heating in a basic environment can undergo, besides a demolition action, also a dismutation reaction to the corresponding acid and alcohol. This dismutation is an activation of the sugar which, also unintended, makes the sugar suitable to the formation of a stable complex with the ferric hydroxide. The negative side of these synthesis methods is the end product, which is a mixture of products containing ferric hydroxide more or less complexed with sugars at least partly decomposed or modified in an uncontrolled way. In fact, it is apparent that also by carefully carrying out these steps for the formation of the complexes, considering the different hydrolysis, demolition and activation reactions of the sugar which can occur in a concomitant way, it is to be expected, of course, that the end product contains iron complexes with more or less modified different sugars species. Typical of these complexes is the caramel smell which comes with the end product in solution meaning that a partial demolition of the same has been attained.

For example, the patent BE 787662 lies within this class of patents, as it claims a method for the synthesis of complexes obtained by reacting ferric chloride hexahydrate in solution and a sugar included among a low molecular weight dextrin, maltose or glucose with a pH in the range from 11.0-14.0 and at a temperature of 90° C.: during the reaction, a mixture of ferric hydroxides precipitates and simultaneously the sugar is partly hydrolized and dismutated, namely it also undergoes a process which leads to its activation which however, taking place in the presence of trivalent iron, can lead to an important level of hydrolysis products.

Therefore, with this kind of process there is, from one side, the application of a simpler methodology, but on the other side, the process is varying both for the obtainment of ferric hydroxide, which remains partly not dissolved at the end of the reaction, and for the degradation/activation of the sugar. In U.S. Pat. No. 2,820,740, the applied methodology foresees a reaction between the dextran partly hydrolized and ferric chloride or ferric citrate in the presence of sodium carbonate at a temperature varying between 65 and 100° C. There remains some ferric hydroxide, which does not form the complex and which is finally filtered and eliminated. This residue shows that the reaction for obtaining the ferric hydroxide has been carried out in uncontrolled conditions and, as above mentioned, leads to a polymorph mixture of ferric hydroxide.

In the patent GB 1,019,513, a depolimerized sugar, dextran, is used, wherein the aldehyde end group has been eliminated by reduction with NaBH4. The sugar became activated and is able to give a stable complex, even if it is necessary to completely eliminate the boron because of its toxicity.

The ferric salt used is the ferric trichloride, to which a certain quantity of citric acid, which is an iron complexing agent, is added.

In the U.S. Pat. No. 2,885,393, depolimerized dextran is reacted and activated with a ferric chloride solution brought to a pH of 2.3 with sodium carbonate, by heating the whole at 65° C. for 30 minutes.

The U.S. Pat. No. 4,180,567 claims the activation of sugars either through reduction with NaBH4 or through a basic treatment at pH 10.5-11.3 for 1 hours at 95° C.-100° C. Such sugars are reacted with ferric hydroxide dialyzed at high temperature, then the solution is concentrated and the bottom body is filtered.

In the U.S. Pat. No. 4,599,405, a dextran with an average molecular weight equal to 5000 Daltons is reacted with ferric trichloride after the salt solution has been brought to pH 1.7 by slow addition of a $Na_2CO_3$ solution and subsequently NaOH is added up to pH 11.0 over 30 minutes. A suspension is formed, which is heated at 100° C. for about one hour. The solid which does not form the complex is eliminated by centrifugation and then the product is isolated by precipitation with solvents. Also with this method, there is the formation of a mixture of hydrated iron compounds which do not form completely soluble complexes with the sugars. It should be noted that the high temperature used in the formation of the complex, as also observed for other patents, can lead to the partial degradation/activation of the system which can be pointed out by the black colour of the obtained solution and by the caramel smell.

In the U.S. Pat. No. 6,291,440, a complex obtained between ferric hydroxide and hydrogenated dextran with a molecular weight between 700 and 1400 Daltons is claimed.

Dextran purification is carried out by membrane filtration, in order to eliminate both the high molecular weights which are responsible for the anaphylactic reactions and the very low molecular weights which are responsible for the instability of the preparations.

The patent DK 129353 claims a method for forming the complex between iron and a dextran with a maximum molecular weight up to 50000 Daltons, preferably between 1000 and 10000 Daltons. The dextran has the end groups oxidized to the corresponding acid, but the method for obtaining the same is not disclosed.

In the publication of the patent application WO 00/30657 a low weight dextran is claimed, obtained by hydrolysis at pH 1.5 and at 90° C. The dextran is fractionated by ultrafiltration with a cut off of 5000 Daltons and after depolimerization, is further ultrafiltered using a cut off between 350-800 Daltons, in order to eliminate the very low weights. On the obtained dextran, a reduction with $NaBH_4$ is carried out for reducing about the 15% of the end hemiacetal groups, and therefore the oxidation with NaClO of the remaining end groups is carried out. The formation reaction of the complex is carried out at a pH of 1.6 when the iron chloride has been partly neutralized with sodium carbonate. Also for this patent, is not clear why the sugar, in this case the dextran, is added when more than 60% of the ferric chloride has already been transformed in ferric hydroxide.

It is apparent that the presence, from the start, of the sugar not only promotes the complex formation during the transformation of the ferric chloride in ferric hydroxide, but it promotes the complete transformation of the iron salt in ferric hydroxide preventing the precipitation of the partly hydrated iron.

Finally, the patent EP 0150085 claims a dextran with a molecular weight between 2000 and 6030 Daltons oxidized with sodium chlorite which, according to the inventors, oxidizes in a specific way the aldehyde end group differently from what stated by the U.S. Pat. No. 4,370,476 wherein bromine is used for the oxidation and it is stated that also sodium hypobromite, sodium bromite, chlorine, iodine, sodium hypochlorite, sodium chlorite are likewise effective in the oxidation of the end groups of the dextran.

DESCRIPTION OF THE INVENTION

The aim of the present invention relates to a production process of trivalent iron complexes with polyhydroxylated compounds, such as the mono-, di- or polysaccharide sugars. The process includes different steps, the first of which consisting of the activation of the sugar. It is known since long that the sugars having an aldehyde end group, also in form of hemiacetal form, can be oxidized through different methods using bromine or other reagents, such as bromites, chlorites, hypochlorites, hypoiodites, or bromides and gaseous halogens, such as chlorine gas in a basic environment. All these reagents are either difficult to handle because of their dangerousness, see bromine and chlorine, or unstable, or they give rise to aspecific oxidation reactions, by oxidizing aldehydes and primary alcohols.

In the patent GB 289280, only the oxidation of glucose and galactose is described, using bromides or iodides and chlorine in a strongly alkaline environment. The reaction is carried out at a temperature lower than 15° C. for avoiding the formed bromine from escaping from the environment. The chlorine is added all at once, this means that the environment itself becomes saturated with chlorine, or rather hypochlorite, and therefore both the bromine originating from the oxidation of the bromide, and the hypochlorite co-exist as sugar oxidants. This hinders a clean and complete reaction, as the hypochlorite is able to oxidize also the primary alcohol on the carbon in 6-position giving the glutaric acid and at the same time can hydrolize the complex sugars, such as the polysaccharides. In the U.S. Pat. No. 6,498,269, the oxidation of even complex sugars in a strongly alkaline environment is reported, through treatment with halogen, generally gaseous chlorine, in the presence of a catalyst of the oxyammonium halide type, by obtaining a diacid as main product.

Surprisingly, we have found that if the use of bromine as an oxidizing agent is desired, its dangerousness and handling difficulty are overcome by producing such oxidizing agent in situ, slowly introducing sodium hypochlorite instead of gaseous chlorine in a strongly acid environment in the aqueous solution containing an alkaline or alkaline earth bromide and the sugar, at a pH between 5.0 and 11.0. The sugar activation is advantageously industrially carried out because of the easiness of handling of the reagents and the repeatability of the reaction itself, as the oxidizing agent is produced in situ by treating a small quantity of an alkaline or alkaline earth metal bromide with an alkaline or alkaline earth metal hypochlorite, preferably sodium hypochlorite at a pH in the range between 5.0 and 11.0, preferably between 7.0 and 9.0. In this way, the handling of reagents which require particular precautions, such as bromine, is avoided, and the activation reaction is further carried out in controlled conditions, in fact the bromide quantity used is between 0.5% and 5% by weight of the sugar to be activated, therefore the bromine quantity which is formed and is found in the reaction environment during the activation phase is really low with respect to the quantity of sugar to be activated. The bromine quantity needed for the sugar activation is produced instant by instant from the addition of the alkaline or alkaline earth hypochlorite, which is used in a stoichiometric quantity with respect to the number of end aldehydes according to the reactions:

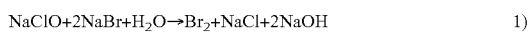
$$NaClO+2NaBr+H_2O \rightarrow Br_2+NaCl+2NaOH \qquad 1)$$

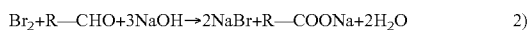
$$Br_2+R-CHO+3NaOH \rightarrow 2NaBr+R-COONa+2H_2O \qquad 2)$$

Surprisingly, contrary to what happening by heating the sugar in an alkaline environment with the dismutation of the aldehyde group and the concomitant partial decomposition of the sugar, by our method an univocal and absolutely clean reaction is obtained, with the specific oxidation of the end aldehyde.

In fact, by using stoichiometric quantities of hypochlorite with respect to the aldehyde end groups and adding it slowly, such that all the added hypochlorite only serves for the bromide oxidation and an excess of hypochlorite in solution is never present, the specific oxidation of the aldehyde group is obtained, maintaining unchanged the remaining chemical structure of the sugar used. The oxidation reaction is controlled through the pH adjustment. In fact, as the acid formation leads to a remarkable lowering of the pH and the consumption of hypochlorite, it is sufficient to add the hypochlorite itself such that the pH is not lowered below 6.0 and the value of 10.0 is not exceeded. From the $^1$H NMR spectrum which relates to the maltose oxidation, depicted in FIG. 1, it can be noted the univocity of the structure obtained after the activation reaction carried out according to the method of the present invention. Should, on the contrary, an excess of hypochlorite also be present, in addition to bromine in the reaction environment, oxidation secondary reactions could occur, which would relate to other parts of the end sugar and to depolimerization phenomena. Therefore, it is important to maintain the reaction pH in the range between 5.0 and 12.0, preferably, between 7.0 and 9.0, since in this pH range the bromine consumption takes place at a high rate leading to the oxidation of the aldehyde end group. With polisaccharide sugars, such as dextrins and dextrans, the activation reaction is carried out using, for the stoichiometric calculation, the average molecular weight or rather the value of dextrose equivalents, which shows the glucose equivalents corresponding with the aldehyde end groups. In this way, the reaction is carried out in strictly alkaline conditions and is of a simple repeatability. If a quantity of alkaline or alkaline earth hypochlorite different from the stoichiometric quantity is added, a partial sugar activation can be obtained, if a lower quantity of hypochlorite is used, with negative consequences on the stability of the end complex, otherwise, if a stoichiometric excess of hypochlorite is used, a further oxidation with a partial demolition of the end sugar can be obtained, in addition to the described activation. Furthermore, in this latter case, a depolimerization of the sugar itself with formation of oligomers and low molecular weights can be simultaneously obtained. In both cases, the end product is not homogeneous, being a mixture of sugars with a different chemical structure. The disadvantage of using a similar mixture of activated sugars is the obtainment of iron complexes with non homogeneous structure and stability.

In the ambit of the present invention, the preferred bromide is sodium bromide and the preferred hypochlorite is sodium hypochlorite.

The second step of the process relates to the complexation reaction of the sugar activated with a proper salt of water soluble trivalent iron; the preferred salt for the execution of the present invention is the iron trichloride hexahydrate in a concentrated aqueous solution. For the good result of the complexation reaction, it is necessary to initially mix the activated sugar with the trivalent iron salt before the increase of the pH, such that the sugar and the water can immediately stabilize the trivalent iron facilitating the complete hydration reaction of the iron. This is pointed out in that, during the formation step of the iron hydroxide by slow addition of a base of alkaline metal, the precipitation of the iron hydroxide itself never occurs, and the reaction always appears homogeneous. Only in the case of gluconic acid, when used in a concentrated solution at a pH between 3.0 and 4.0, there is the precipitation of the ferric hydroxide already complexed by the sugar, as in fact for obtaining the complete solubilization of the precipitate it is sufficient to increase the pH between 9.0 and 10.0. This fact is important since in no case a solid is precipitated or a bottom body is left, as in the case of processes wherein the sugar is added after an even partial increase of pH in order to obtain ferric hydroxide, or after complexation of the isolated ferric hydroxide. The addition of ferric salt to the early activated sugar solution does not lead to depolimerization phenomena of the sugar itself, even if the initial pH is very acid, because the solution temperature is maintained below 60°0. This step is critical, because the increase rate of the pH for the obtainment of the ferric hydroxide must be suitable for carrying out the iron hydration reaction and, at the same time, promoting the formation of an initial Fe-sugar complex, so as to allow the completion of the hydration reaction of the iron itself without hydroxide precipitation.

The third step of the process consists of the purification of the ferric hydroxide-sugar complex, even if such complex is still not been stabilized by heating. Surprisingly, we have found that once the pH of the starting solution containing the activated sugar and the iron has been increased in the range between 6.0 and 12.0, the ferric hydroxide-sugar complex, even if not yet stabilized, can be ultrafiltered through a membrane with a proper cut-off. This process allows to remove all the salts formed during the hydration reaction of the iron, by obtaining a compound which can also be stored for a long time, waiting to be subjected to following stabilization reactions.

Following to the purification, the trivalent iron-sugar complex is subjected to the stabilization step of the complex, wherein there is the modification of the ferric hydroxide in ferric oxy-hydroxide. This treatment takes place at a temperature between 60° C. and 100° C. for a period between 1 and 4 hours at a pH between 9.0 and 12.0. The stabilization treatment can also be carried out before the purification treatment through ultrafiltration, obtaining the same result. In particular, this occurs in the production of the trivalent iron complex with the activated glucose.

The complexes thus obtained and divided in glass vials or bottles can be successively sterilized by heating in autoclave at 125° C. for 30 minutes without undergoing any stability modifications of the end complex. Finally, before the division in vials, the complexes between ferric hydroxide and sugar can be blended with other sugars in a desired proportion resulting, in some cases, in a further stabilization of the complex.

DETAILED DESCRIPTION OF THE INVENTION

Figure 1:
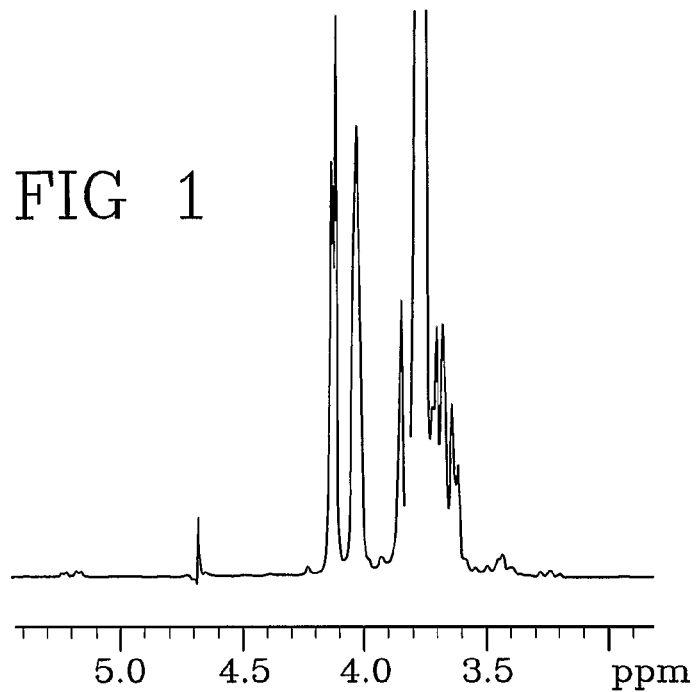
FIG. 1 is a depiction of the 1H NMR spectrum relating to glucose oxidation.

The aim of the present invention consists of a process for the preparation of complexes of trivalent iron ($Fe^{3+}$) with mono-, di- and polysaccharide sugars, complexes characterized by a good physical-chemical stability over time, low toxicity, use safety also by injection and a good bioavailability.

Said process, characterized by execution easiness and safety, consists of four steps:
1. activation of mono-, di- or polysaccharide sugar;
2. complexation of the activated sugar with ferric hydroxide generated in solution;
3. purification of the ferric hydroxide/sugar complex still not stabilized;
4. stabilization of the ferric hydroxide/sugar complex.

The process is completed with the possible mixing of the obtained complex with other sugars, a mixing which imparts a further stabilization to the complex, and with the packaging of the medicinal speciality through sterilizing filtration, subdivision of the solution in glass vials or bottles and final sterilization in autoclave at 125° C. for 30 minutes.

Preferred sugars in the execution of the present invention are: glucose, maltose, lactose, maltodextrins and dextrans.

The sugar activation is carried out by oxidation with nascent bromine. by dissolving the sugar in purified water at a concentration between 10% and 50% by weight, adding an alkaline or alkaline earth bromide, preferably Sodium bromide, in a quantity between 0.5% and 5% by weight based on the sugar weight, bringing the pH of the solution to a value between 5.0 and 11.0, preferably between 7.0 and 9.0, with sodium hydroxide and adding under stirring at a temperature between 10° C. and 60° C. in a period between 2 and 4 hours an aqueous solution containing a weighed stoichiometric quantity of an alkaline or alkaline earth metal hypochlorite, preferably sodium hypochlorite, with respect to the aldehyde end groups existing in the sugar. Preferred in the ambit of the invention are sodium hypochlorite aqueous solutions containing about 12% by weight of active chlorine. Throughout the activation reaction of the sugar, the pH value is controlled and maintained in the fixed range, preferably between 7.0 and 9.0, by adjusting the addition rate of the hypochlorite. At the end of the reaction, to the solution of activated sugar a concentrated aqueous solution of a ferric salt is added under stirring, at a temperature between 15° C. and 60° C., so as the trivalent iron/sugar weight ratio is in the range between 1:0.5 and 1:4. All the water soluble trivalent iron salts can be used, the greatly water soluble ferric chloride hexahydrate being preferred in the execution of the invention, whereby very concentrated aqueous solutions can be obtained, for example aqueous solutions containing 40% by weight of ferric chloride.

After the addition of the ferric salt solution, to the mixture under constant stirring an aqueous solution of sodium carbonate is added, preferably at 15% w/v, in a period between 1 and 6 hours with, so as to slowly increase the pH never exceeding the value between 2.3 and 2.7.

When this pH range has been reached, the stirring of the solution is continued for a time between 15 and 60 minutes and only subsequently, in a time between 1 and 2 hours, the pH of the solution is brought to values between 8.0 and 12.0 by addition of an aqueous solution of sodium hydroxide, preferably at concentrations between 15% and 30% w/w.

The solution of the trivalent iron-sugar complex thus obtained is subjected to purification with removal of the salts and all the products with a low molecular weight, by subjecting it to a membrane ultrafiltration with a cut-off between 3000 and 5000 Daltons for the mono- and disaccharide sugars, such as glucose, maltose, lactose, and with a cut-off between 400 and 50000 Daltons for the polysaccharide sugars, such as dextrins and dextrans.

The ferric hydroxide-sugar complex thus purified is stabilized by heating of the solution which contains the same at a temperature between 60° C. and 100° C., preferably between 75° C. and 95° C. for a time between and 4 hours at a pH between 9.0 and 12.0. The purified and stabilized solution can be stored for a long time in a cooled environment and when one desires to use it for the preparation of medicinal specialities, it has to be heated at a temperature between 60° and 100° C., preferably between 75° C. and 95° C. for a time between 3 and 6 hours and therefore the end product can be isolated in different ways.

For example, it can be isolated in form of a powder through spraying or freeze-drying, after having adjusted, if necessary, the pH of the solution at values between 4.5 and 7.0. Otherwise, it is possible to add the solution of the stabilized and purified complex with a further sugar quantity, also different from the one present in the complex, which further stabilizes the solution, which can be divided in glass vials or bottles which are then sterilized at 125° C. for 30 minutes, preferably at 121° C. for 20 minutes, or it can be freeze-dried, obtaining the end product in form of a powder.

In an advantageous embodiment, the process for the preparation of trivalent iron complexes with mono-, di- and polysaccharide sugars includes the activation of the sugar. The sugar is obtained by dissolving the sugar in purified water at a concentration between 10% and 50% by weight, adding an alkaline or alkaline earth bromide in a quantity between 0.5% and 5% by weight based on the sugar weight, bringing the pH of the solution to a value between 5.0 and 11.0 and adding under stirring in a time between 2 and 4 hours, at a temperature between 10° C. and 60° C., an alkaline or alkaline earth metal hypochlorite in aqueous solution in a stoichiometric quantity with respect to the aldehyde end groups present in the sugar, if not branched; in the specific case of the dextran, a hypochlorite quantity corresponding with the double of the moles is used.

Subsequently, the activated sugar complexation, is obtained by adding the solution of activated sugar under stirring, at a temperature between 15° C. and 60° C., with an aqueous solution of a ferric salt, such that the weight ratio of iron to sugar is between 1:0.5 and 1:4 (from 1:0.5 to 1:5), adding in a time between 1 a 6 hours, an aqueous solution of sodium carbonate in order to bring the pH to a value between 2.3 and 2.7, maintaining constant the pH in this range of values for a time between 15 and 60 minutes, and therefore bringing the pH to values between 8.0 and 12.0 by addition of a sodium hydroxide aqueous solution. Subsequently, the complex between ferric hydroxide and sugar is purified by ultrafiltration of the solution. Finally, the complex is stabilized by heating of the ultrafiltered solution at a temperature between 60° C. and 100° C. for a time between 1 and 4 hours at a pH between 9.0 and 12.0. In the case of dextran, the heating takes place for a minimum of 5 hours. For example, the sugars are selected from glucose, maltose, lactose, maltodextrins and dextrans. The bromide is sodium bromide. The pH of the activation reaction of the sugar is between 7.0 and 9.0. The hypochlorite is sodium hypochlorite and the ferric salt is ferric chloride hexahydrate. The stabilization temperature of the complex is between 75° C. and 95° C. For example, the ultrafiltration is carried out with a membrane with a cut-off between 3000 and 5000 Daltons for the glucose, maltose and lactose, while for maltodextrins and dextrans with a cut-off 400 in order to remove the salts and with a cut-off between 30000 and 50000 Daltons in order to remove the low molecular weights.

For example, the stabilization treatment of the trivalent iron-gluconic acid complex is carried out before the purification treatment. The complexes which can be obtained are for example ferric gluconate, the complex between iron hydroxide and maltose, the complex between iron hydroxide and lactose, the complex between iron hydroxide and maltodextrins, the complex between iron hydroxide and dextran.

Figure 2:
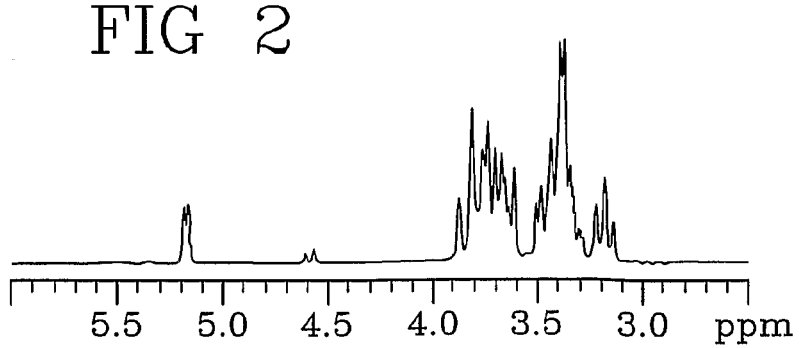
FIG. 2 is a depiction of the 13C NMR spectrum relating to glucose oxidation.

The enclosed FIG. 1 relates to activated glucose, while the enclosed FIG. 2 relates to glucose as such.

The following examples constitute a further illustration of the aim of the invention and are not to be intended as a limitation thereof.

EXAMPLE 1

Preparation of Ferric Gluconate 50 grams of glucose are dissolved under stirring in 740 ml of purified water, and to the obtained solution 0.5 g. of sodium bromide are added by simultaneously bringing the pH of the solution to a value between 7.0 and 9.0 with a sodium hydroxide solution.

Over two hours, 164 g. of 12% active chlorine sodium hypochlorite solution are added, a quantity corresponding with a molar weight 1:1 with respect to the glucose, by maintaining the pH value between 7.0 and 9.0 and, at the end of the addition, the stirring is continued for other 30 minutes. The control of the accomplished execution is carried out through HPLC or through polarimetric readings. The oxidation of glucose to gluconic acid is obtained, as it can be verified by the 13C NMR spectrum depicted in FIG. 1.

The solution of gluconic acid is brought to a temperature between 16° C. and 20° C. and is added with 416 g. of a 40% ferric trichloride solution at 40% by weight (iron/sugar ratio=1:0.87 w/w). The stirring is continued for a complete homogenization of the solution and in about two hours a 15% w/v sodium carbonate solution is added, until bringing the pH at a value between 2.3 and 2.7.

Once such value has been reached, the solution is maintained under stirring for a time of 30 minutes by controlling that the pH remains between 2.3 and 2.7. Subsequently, with a solution of sodium hydroxide at 15% w/v, the pH is brought to 11.0±0.5 over 1 hour, and during the increase of the pH between 3.0 and 4.0 the formation of a precipitate comprised of ferric hydroxide-gluconic acid complex occurs, which tends to solubilize while the pH increases until a complete solubilization at a pH above 9.0.

A brown-coloured solution is obtained, which has no solids in suspension and is brought to the temperature of 85±2° C. and maintained under this conditions for 2 hours. At the end of the stabilization reaction of the complex, the obtained solution is purified from the salts through an ultrafiltration system equipped with a membrane with a cut-off of 3000 Daltons.

The resulting solution purified from the salts, brought to a pH of 10.5±5, can be stored in a cooled environment and, before its pharmaceutical use, is again heated at a temperature of 90±2° C. for a period of 4 hours. The ferric gluconate is isolated by spraying, obtaining a yield higher than 85%, computed on the starting iron.

The physical-chemical features of the complex are the following:
average Molecular Weight (Mw)=43347 Daltons
numerical Molecular Weight (Mn)=30495 Daltons
polydispersibility=1.4
Fe3+ Content=48.6%

The molecular weights have been determined using the gel-permeation chromatography method, described on page 1065 by the United States Pharmacopoeia (USP) 28' Ed., which uses 2 columns in series TOSO HAAS column TSK-GEL G5000PWXL 30 cm×7.8 cm ID+TOSO HAAS column TSK-GEL 2500 PWXL 30 cm×7.8 cm ID and dextrans with a known average molecular weight Mw as a standard, and with the following molecular weights at the top of the peak, expressed in Daltons: 4410, 9890, 21400, 43500, 66700, 123500, 196300, 276500.

EXAMPLE 2

Preparation of Ferric Gluconate

The ferric gluconate complex can be obtained using the same methodology of the example 1, starting from commercial gluconic acid and ferric chloride.

24.5 grams of sodium gluconate are dissolved in 120 ml of purified water and to the obtained solution 205 g. of a 40% wt ferric chloride solution (iron/sugar ratio=1:0.87 w/w), keeping under stirring until a complete homogenisation of the reaction mixture is reached.

The solution temperature is brought between 16° C. and 20° C. and over 2 hours a 15% w/v sodium carbonate solution is added, to bring the pH of the solution at values between 2.3 and 2.7.

When such value has been reached, the solution is maintained under stirring for a period of 30 minutes, by controlling that the pH remains between 2.3 and 2.7.

Subsequently, with a 15% w/v sodium hydroxide solution, the pH is brought to 11.0±0.5 over 1 hour, during this step with a pH between 3.0 and 4.0 there is the formation of a precipitate, formed by a ferric hydroxide-gluconic acid complex, which solubilizes while the pH is increased until a complete solubilization at a pH above 9.0.

A brown-coloured solution is obtained, which has no solids in suspension and is brought to the temperature of 85±2° C. and maintained under this conditions for 2 hours. At the end of the stabilization reaction of the complex, the obtained solution is purified from the salts through an ultrafiltration system equipped with a cut-off membrane of 3000 Daltons.

The resulting solution purified from the salts, brought to a pH of 10.5±5, can be stored in a refrigerated environment and, before its pharmaceutical use, is again heated at a temperature of 90° C. for a period of 4 hours. The ferric gluconate is isolated as such by freeze-drying, obtaining a yield above 85% computed on the starting iron. The physical-chemical features of the complex, with the molecular weights determined according to the methodology described in the example 1, are the following:
average Molecular Weight (Mw)=53745 Daltons
numerical Molecular Weight (Mn)=30976 Daltons
polydispersibility=1.7
$Fe^{3+}$ Content=48.5%

EXAMPLE 3

Preparation of the Ferric Hydroxide/Maltose Complex 60 grams of maltose are dissolved in 200 ml of purified water, to the solution thus obtained 0.6 g. of sodium bromide are added and the pH of the solution is brought to a value between 7.0 and 9.0 with a sodium hydroxide aqueous solution.

Over two hours, 98.5 g. of 12% active chlorine sodium hypochlorite are added, corresponding with the stoichiometric quantity with respect to the aldehyde end groups, by maintaining the pH value between 7.0 and 9.0. At the end of the addition, the stirring is continued for 30 minutes and the control of the accomplished activation is carried out through HPLC by detecting the residual maltose and activated maltose ratio.

To the activated maltose solution, brought at a temperature between 16° C. and 20° C., 257 g. of a 40% wt (iron/sugar ratio=1:1.7 w/w) are added continuing the stirring until a complete homogenization of the reaction mixture. Therefore, to the obtained solution a 15% w/v sodium carbonate solution is added over 3 hours, so as to slowly bring the pH at a value between 2.3 and 2.7.

When this value has been reached, the solution is maintained under stirring and in these conditions over 15 minutes, by checking that the pH value remains between 2.3 and 2.3, and therefore the pH value is brought to 10.5±0.5 over 1 hour, adding a 15% w/v. sodium hydroxide solution. The precipitation of iron hydroxide never occurs, neither in form of a complex. The obtained solution is purified from the salts through an ultrafiltration system equipped with a membrane with a cut-off of 3000 Daltons.

The resulting solution purified from the salts is brought to a pH of 11.5±0.5 and heated at a temperature of 75° C.±2 for a period of 2 hours, then the complex is isolated by freeze drying.

The physical chemical features of the complex, with the molecular weights determined according to the methodology described in the example 1, are the following:
  average Molecular Weight (Mw)=53655 Daltons
  numerical Molecular Weight (Mn)=35988 Daltons–Polydispersibility=1.5
  $Fe^{3+}$ Content=41.4%

EXAMPLE 4

Preparation of the Ferric Hydroxide-Lactose Complex 50 grams of lactose are dissolved in 250 ml of purified water and to the obtained solution 0.5 g. of sodium bromide are added bringing the pH to a value between 7.0 and 9.0 with a sodium hydroxide solution. Over two hours, 98.5 g. of 12% active chlorine sodium hypochlorite are added, corresponding with the stoichiometric quantity with respect to the aldehyde end groups, maintaining the pH value between 7.0 and 9.0. At the end of the addition, the stirring is continued for 30 minutes and the control of the accomplished activation is carried out through HPLC by detecting the residual lactose and activated lactose ratio.

To the activated lactose solution, brought at a temperature between 16° C. and 20° C., 300 g. of a 40% wt iron chloride solution (iron/sugar ratio=1:1.7 w/w) are added continuing the stirring until a complete homogenization of the reaction mixture. Therefore, to the obtained solution a 15% w/v sodium carbonate solution is added over 3 hours, so as to slowly bring the PH at a value between 2.3 and 2.7.

When this value has been reached, the solution is maintained under stirring and in these conditions over 15 minutes, by checking that the pH value remains between 2.3 and 2.7, and therefore the pH value is brought to 10.5±0.5 over 1 hour, adding a 15% w/v sodium hydroxide solution. The precipitation of iron hydroxide never occurs, neither in form of a complex. The obtained solution is purified from the salts through an ultrafiltration system equipped with a membrane with a cut-off of 3000 Daltons.

The resulting solution purified from the salts is brought to a pH of 11.0±0.5 and heated at a temperature of 75±2° C. for a period of 2 hours and then after cooling and correction of the pH value at 7, the active substance is isolated by spraying.

The physical-chemical features of the complex, with the molecular weights determined according to the methodology described in the example 1, are the following:
  average Molecular Weight (Mw)–65571 Daltons–numerical molecular weight (Mn)=40669 Daltons polydispersibility=1.6
  $Fe^{3+}$ Content=49.6%

EXAMPLE 5

Preparation of the Ferric Hydroxide-Polymaltose Complex 70 grams of maltodextrins, characterized by a value of dextrose equivalents equal to 19, are dissolved in 200 ml of purified water and to the obtained solution 1.4 g. of sodium bromide are added.

The pH of the solution is brought to a value between 7.0 and 9.0 with a sodium hydroxide solution and over 2 hours, 48.66 g of 12% w/v active chlorine sodium hypochlorite are added, maintaining the pH within the fixed limits. At the end of the addition, the stirring is continued for 30 minutes and the accomplished activation is controlled through a HPLC-GPC technique.

To the activated maltodextrin solution, brought at a temperature between 16° C. and 20° C., 300 g. of a 40% w/v iron chloride solution (iron/sugar ratio=1:1.7 w/w) are added and the stirring is continued until a complete homogenization of the reaction mixture.

Over a period of 5 hours, an aqueous 15% w/v sodium carbonate solution, required for bringing the pH at a value between 2.3 and 2.7 is added under stirring, and when this value has been reached the solution is maintained in these conditions over 15 minutes, by checking that the pH value remains between 2.3 and 2.7.

With a 15% w/v sodium hydroxide solution, the pH is brought to the value of 9.0±0.5 over 1 hour. The precipitation of iron hydroxide never occurs, neither in form of a complex.

The obtained solution is purified from the salts through an ultrafiltration system equipped with a membrane with a cut-off of 30000 Daltons.

The resulting solution is heated at the temperature of 92±2° C. for a time of 3 hours and at a pH of 10.8±0.2.

The cooled solution is brought to pH 6.0±0.5 and then the product is isolated at the dry state through spraying.

The physical-chemical features of the complex are the following:
  average Molecular Weight (Mw)=167319 Daltons
  numerical Molecular Weight (Mn)=69319 Daltons–Polydispersibility=2.4
  $Fe^{3+}$ Content=34.8%

The molecular weights have been determined using the gel-permeation chromatography method which uses a column TOSO HAAS, column model TSK-GEL G5000PWn 30 cm×7.8 cm ID and, as a standard, dextrans with the following average molecular weights Mw expressed in Daltons: 48600, 80900, 147600, 273000, 409800, 667800.

EXAMPLE 6

Preparation of Ferric Hydroxide-Clextran Complex 17.5 grams of dextran, with an average molecular weight between 2000 and 7800, are dissolved in 65 ml of purified water and to the obtained solution 0.34 g. of sodium bromide are added. The solution is heated at 50° C. and the pH is brought at a value between 7.0 and 9.0 with a sodium hydroxide solution.

4.14 g. of 12% w/v active chlorine sodium hypochlorite (2 mMoles), corresponding with the double of the dextran moles with an average molecular weight of 5000 Da are added over two hours, maintaining the pH value between 7.0 and 9.0.

To the activated dextran solution, brought to the temperature of 40° C. or 30° C., 75 g of a 40% w/v iron chloride solution (iron/sugar ratio=1:2 w/w) are added, continuing the stirring until a complete homogenization of the reaction mixture.

A 15% w/v sodium carbonate aqueous solution, required for bringing the pH at a value between 2.3 and 2.7 is added over two hours, and when such value has been reached, the reaction mixture is maintained under these conditions for 30 minutes, controlling that the pH remains constant.

With a 15% w/v sodium hydroxide aqueous solution, the pH value is brought to 11.5±0.2 over 1 hour and the obtained solution is heated at 95±2° C. for three hours and thirty minutes, therefore, after cooling, is purified from the salts through an ultrafiltration system equipped with a membrane with a cut-off of 400 Daltons, in order to remove the salts contained.

Once desalted, the solution is maintained at a pH 11.0±0.2, heated at the temperature of 95±2° C. for a period of at least 5 hours and therefore cooled at room temperature. The pH of the solution is brought to the value of 6.0±0.2 and after addition of phenol, stored in sterile containers.

The active substance can also be isolated by spraying. The reaction yield is above 85% with respect to the starting iron. The physical-chemical features of the complex, with the molecular weights determined according to the methodology described in the example 5, are the following:
average Molecular Weight (Mw)=226392 Daltons
numerical Molecular Weight (Mn)=125590 Daltons
polydispersibility=1.8
$Fe^{3+}$ Content=36.7%

EXAMPLE 7

Preparation of Ferric Hydroxide-Dextran Complex 17.5 grams of dextran, with an average molecular weight between 2950 and 7800, are dissolved in 65 ml of purified water and to the obtained solution 0.34 g. of sodium bromide are added. The solution is heated at 50° C. and the pH is brought at a value between 7.0 and 9.0 with a sodium hydroxide solution.

4.14 g. of 12% w/v active chlorine sodium hypochlorite, corresponding with the double of the dextran moles with an average molecular weight of 5000 Da are added over two hours, maintaining the pH value between 7.0 and 9.0.

To the activated dextran solution, brought to the temperature of 50° C., 42.4 g. of a 40% w/v iron chloride solution (iron/sugar ratio=1:3 w/w) are added, continuing the stirring until a complete homogenization of the reaction mixture.

A 15% w/v sodium carbonate aqueous solution, required for bringing the pH at a value between 2.3 and 2.7 is added over a period between two and five hours, and when such value has been reached, the reaction mixture is maintained under these conditions for 30 minutes, controlling that the pH remains constant.

With a 15% w/v sodium hydroxide aqueous solution, the pH value is brought to 11.5±0.2 over 1 hour and the obtained solution is purified from the salts through an ultrafiltration system equipped with a membrane with a cut-off of 400 Daltons: in this case, only the existing salts are removed, not the unreacted excess of dextran. If the removal of all the uncomplexed dextran is desired, then it is necessary to use a membrane with a cut-off of 50000 Daltons.

Once desalted, the solution is maintained at a pH 11.5±0.2, heated at the temperature of 95±2° C. for a period of at least 5 hours and therefore cooled at room temperature. The pH of the solution is brought to the value of 6.0±0.2 and therefore the active substance is isolated through spraying. The reaction yield is above 85% with respect to the starting iron.

If one desires to maintain the active substance in a solution, phenol is added and the storage is carried out at 20° C. in sterile containers.

The physical-chemical features of the complex, with the molecular weights determined according to the methodology described in the example 5, are the following:
average Molecular Weight (Mw)=205127 Daltons
numerical Molecular Weight (Mn)=151276 Daltons
polydispersibility=1.4

EXAMPLE 8

Preparation of the Ferric Gluconate Stabilized with Sucrose

To the ferric gluconate solution stabilized and purified from the salts, obtained according to the procedures described in the examples 1 and 2, 806 g. of sucrose are added under stirring, a quantity with which the iron/sucrose ratio equal to 1:15.6 is reached.

The solution thus obtained is freeze-dried, giving the ferric gluconate stabilized with sucrose.

EXAMPLE 9

Preparation of the Ferric Hydroxide/Maltose Complex Stabilized with Sucrose

To the solution containing the ferric hydroxide/activated maltose complex, after purification and stabilization carried out according to the procedure described in the Example 3, 458 g. of sucrose are added under stirring, a quantity with which an iron/sucrose ratio equal to 1:15 is reached. The solution thus obtained is freeze-dried, giving the stabilized complex of ferric hydroxide-maltose in a solid form.

The invention claimed is:

1. A process for the preparation of an activated sugar Fe(III)-complex, wherein said sugar is selected from the group consisting of mono- or disaccharide sugars, said process comprising:
 (a) providing a solution comprising said sugar to be activated and bromine, characterized in that said bromine is produced in situ in the presence of said sugar to be activated at a pH in the range from 5 to 12 through the addition of stoichiometric quantities with respect to the aldehyde end groups of said sugar of a hypochlorite of an alkaline or earth alkaline metal to a solution comprising said sugar to be activated and a bromide of an alkaline or earth alkaline metal, wherein the addition of hypochlorite is carried out instant-by-instant in a way such that all the added hypochlorite only serves for the bromide oxidation and an excess of hypochlorite in solution is never present, thereby producing an activated sugar solution wherein the end aldehyde group is oxidized,
 (b) adding a water soluble ferric salt to the activated sugar solution, such that the resulting solution contains the activated sugar and the iron (III) salt in an iron to sugar weight ratio between 1:0.5 and 1:5, whereafter the pH of the solution is controlled at a value between from 2.3 to 2.7 by adding a sodium hydrogencarbonate or a sodium carbonate solution in a time between 1 and 6 hours;
 (c) bringing the pH of the solution as per step (b) subsequently to a value between 8 and 12, to give a solution containing the Fe (III)-activated sugar complex, and (d) purifying the Fe (III)-activated sugar complex.

2. The process according to claim 1, wherein the pH in step (a) is between 6 and 11.

3. The process according to claim 2, wherein the pH in step (a) is between 7.0 and 9.0.

4. The process according to claim 1, wherein, in step (a), the hypochlorite is sodium hypochlorite and the bromide is sodium bromide.

5. The process according to claim 4, wherein said sugar to be activated is selected from the group consisting of glucose, maltose, and lactose.

6. The process according to claim 1, wherein the solution in step (a) is an aqueous solution including said sugar to be activated in a quantity between 10 and 50% by weight, based on the weight of the solution.

7. The process according to claim 6, wherein the quantity of bromide in step (a) is between 0.5 and 5% by weight, based on the total weight of said sugar to be activated.

8. The process according to claim 1, wherein the hypochlorite added in step (a) is in an aqueous solution containing about 12% by weight of active chlorine.

9. The process according to claim 1, wherein said ferric salt in step (b) is iron trichloride hexahydrate.

10. The process according to claim 1, wherein the solution in step (b) contains the activated sugar and the iron (III) salt in the iron to sugar weight ratio from 1:0.5 to 1:4.

11. The process according to claim 1, wherein the pH of the solution in step (b) is controlled by adding a sodium hydrogencarbonate solution containing 15% w/v sodium hydrogencarbonate.

12. The process according to claim 1, wherein the pH of the solution as per step (b) is subsequently brought in step (c) to the value between 8 and 12 through the addition of a sodium hydroxide solution.

13. The process according to claim 1, wherein the purification in step (d) is carried out by ultrafiltration with a membrane having a cut-off between 3000 and 5000 Daltons.

14. The process according to claim 13, wherein the Fe (III)-activated sugar complex as per step (c) or (d) is stabilized in a further step (c') or (e) by heating of the solution containing the same at a temperature between 60° C. and 100° C., for a period between 1 and 4 hours at a pH between 9.0 and 12.0.

15. The process according to claim 14, wherein the Fe (III)-activated sugar complex is selected from the group consisting of iron glucose, iron lactose and iron maltose stabilized with sucrose.

16. Fe(III) and activated sugar complex obtainable according to a preparation process according to claim 1.

17. A pharmaceutical composition comprising the Fe(III)-activated sugar complex according to claim 16.

18. A method of treating functional deficiency in patients suffering from a renal chronic failure, bad absorption of the iron due to intestinal diseases, chronic blood loss together with erythropoietin and constitutional anemia, comprising administering the Fe (III)-activated sugar complex pharmaceutical composition of claim 17.

19. The process according to claim 2, wherein the pH in step (a) is between 7 and 10.

20. The process according to claim 14, wherein said Fe (III)-activated sugar complex as per step (c) or (d) is stabilized in a further step (c') or (e) by heating of the solution containing the same at a temperature between 75° C. and 95° C.

* * * * *